US00PP23609P3

(12) United States Plant Patent
Zaiger et al.

(10) Patent No.: US PP23,609 P3
(45) Date of Patent: May 21, 2013

(54) PEACH TREE NAMED 'ASPEN WHITE'

(50) Latin Name: *Prunus persica*
Varietal Denomination: Aspen White

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 303 days.

(21) Appl. No.: 12/930,510

(22) Filed: Jan. 10, 2011

(65) Prior Publication Data

US 2012/0180171 P1 Jul. 12, 2012

(51) Int. Cl.
*A01H 5/00* (2006.01)

(52) U.S. Cl.
USPC ..... Plt./195

(58) Field of Classification Search ..... Plt./195
See application file for complete search history.

*Primary Examiner* — Kent L Bell

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Regular and heavy production of large size fruit.
3. Fruit with firm white flesh, good handling and shipping qualities.
4. Fruit with very good, mild, sweet flavor.
5. Fruit with attractive red skin color.

1 Drawing Sheet

Botanical classification: *Prunus persica.*

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

2. Prior Varieties

Among the existing varieties of peach, nectarines and proprietary seedlings, which are known to us, and mentioned herein, 'Honey Kist' Nectarine (U.S. Plant Pat. No. 9,333), 'May Glo' Nectarine (U.S. Plant Pat. No. 5,245) and our proprietary seedling selections '12GA1100', '7LL330' and '396LN233'.

STATEMENT REGARDING FEDERALLY SPONSORED RESEARCH AND DEVELOPMENT

Not applicable.

ORIGIN OF THE VARIETY

A new and distinct variety of peach tree (*Prunus persica*) was originated by us in our experimental orchards located near Modesto, Calif. as a first generation seedling from seed collected from a cross between our proprietary seedling selections with the field identification numbers '7LL330' and '396LN233'. The seed parent (7LL330) was developed from crosses of the following varieties; 'Honey Kist' Nectarine (U.S. Plant Pat. No. 9,333), 'May Glo' Nectarine (U.S. Plant Pat. No. 5,245) and the proprietary seedling '12GA1100'. The pollen parent (396LN233) was selected from a group of seedlings of unknown parentage. A large group of these first generation seedlings were planted and maintained on their own root system, during which time we recognized the desirable tree and fruit characteristics and selected it in 2005 for asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of peach tree (*Prunus persica*) is of large size, vigorous upright growth and a productive and regular bearer of large size, white flesh, clingstone fruit with very good flavor and eating quality. The fruit is further characterized by having very firm flesh and attractive red skin color. In comparison to its seed parent (7LL330) the fruit of the new variety has white flesh compared to yellow, has pubescent skin compared to glabrous skin and is approximately 6 days earlier in maturity. In comparison to its pollen parent (396LN233) the fruit of the new variety requires approximately 300 hours more winter chilling and is approximately 18 days later in maturity. In comparison to the commercial peach variety 'Sierra Snow' (U.S. Plant Pat. No. 13,527) the tree of the new variety requires approximately 600 hours chilling compared to 800 hours chilling at or below 45° F. and the fruit of the new variety is approximately 10 days earlier in maturity. In comparison to the commercial peach variety 'Sierra Snow' (U.S. Plant Pat. No. 13,527) the tree of the new variety requires approximately 600 hours chilling compared to 800 hours chilling at or below 45° F. and the fruit of the new variety is approximately 10 days earlier in maturity.

PHOTOGRAPH OF THE VARIETY

The accompanying color photographic illustration shows typical specimens of the foliage and fruit of the present new peach variety.

The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 6 year old specimens grown near Modesto, Calif., with color in accordance with Munsell Book of Color.

Tree:

*Size.*—Large, pruned to 3 to 3.5 meters in height and width for economical harvesting of fruit. Varies with different cultural practices.

*Vigor.*—Vigorous, growth of 1.5 meters in height the first growing season. Varies with soil type, fertility and cultural practices.

*Form.*—Upright, usually pruned to vase shape.

*Branching habit.*—Upright, crotch angle approximately 30°, increases with heavy crop load.

*Productivity.*—Productive, thinning and spacing of fruit necessary for desirable marketable size. Number of fruit set varies with climatic conditions during blooming period.

*Bearer.*—Regular, adequate fruit set 4 consecutive years. No alternate bearing observed.

*Fertility.*—Self-fertile.

*Density.*—Medium dense, usually pruned to vase shape to increase air movement and sunlight to the center of the tree to enhance health of tree and improve fruit color.

*Hardiness.*—Hardy in all stone fruit growing areas of California. Tree grown in USDA Hardiness Zone 9. Winter chilling requirement approximately 600 hours at or below 45° F.

Trunk:

*Size.*—Medium. Average circumference 58.4 cm at 31.7 cm above the ground on a 6 year old tree.

*Stocky.*—Medium stocky.

*Texture.*—Medium shaggy, becomes rougher with age.

*Color.*—Varies from 7.5YR 3/2 to 10YR 3/2.

Branches:

*Size.*—Medium. Average circumference 15.2 cm at 1.2 meters above ground. Crotch angle approximately 30°, increases with heavy crop load.

*Surface texture.*—New growth relatively smooth. Mature growth medium rough, roughness increases with age.

*Lenticels.*—Average number 31 in a 25.8 square cm area. Average length 3.7 mm. Average width 1.6 mm. Color varies from 5YR 5/8 to 7.5YR 6/10.

*Color.*—New growth varies from 5GY 6/6 with 7.5R 4/6 where exposed to the sun. Old growth varies from 5YR 2/4 to 7.5YR 3/4, varies with age of growth.

Leaves:

*Size.*—Medium to large. Average length 138.2 cm. Average width 38.5 cm.

*Form.*—Lanceolate.

*Apex.*—Acuminate.

*Base.*—Cuneate.

*Margin.*—Serrate.

*Thickness.*—Medium.

*Surface texture.*—Upper surface relatively smooth, slight indentations over midrib and leaf veins. Lower surface relatively smooth, small ridges created by midrib and pinnate venation. Both surfaces glabrous.

*Petiole.*—Average length 7.4 mm. Average width 1.8 mm. Longitudinally grooved. Surface glabrous. Color varies from 2.5GY 6/6 to 2.5GY 5/6.

*Glands.*—Reniform. Size — small to medium. Average length 1.1 mm. Average diameter 0.6 mm. Average number 5, varies from 4 to 6. Located primarily on the base of the leaf blade and on the upper portion of the petiole. Color — 5GY 6/6.

*Stipules.*—Present, average number 2. Margin — pectinate. Color — 5GY 5/6.

*Color.*—Upper surface varies from 5GY 3/6 to 7.5GY 3/4. Lower surface varies from 5GY 4/4 to 7.5GY 4/4. Midvein color varies from 2.5GY 8/6 to 5GY 7/6.

Flower buds:

*Size.*—Large. Average length 20.8 mm. Average diameter 10.4 mm.

*Hardiness.*—Hardy with respect to California winters.

*Form.*—Conical, becoming elongated before opening.

*Pedicel.*—Average length 4.4 mm. Average width 0.9 mm. Color varies from 5GY 6/6 to 5GY 4/6.

*Color.*—Varies from 5RP 7/10 to 5RP 8/4.

Flowers:

*Date of first bloom.*—Feb. 24, 2010.

*Date of petal fall.*—Mar. 6, 2010, varies slightly with climatic conditions.

*Size.*—Large, showy. Average height 22.6 mm. Average diameter 43.6 mm.

*Petals.*—Normally 5, alternately arranged to sepals. Form — obovate, narrows at point of attachment. Average length 21.8 mm. Average width 17.2 mm. Margin — sinuate. Color varies from 5RP 7/6 to 5RP 9/2. Both surfaces glabrous.

*Sepals.*—Normally 5, alternately arranged to petals. Average length 7.3 mm. Average width 5.9 mm. Shape — triangular. Margin — entire. Surface — upper surface glabrous. Lower surface pubescent. Color — upper surface varies from 2.5GY 4/6 to 5GY 4/6. Lower surface varies from 5RP 3/2 to 5RP 2/4.

*Stamens.*—Average number per flower 46. Average filament length 18.4 mm. Filament color varies from N 9.5/(white) to 5RP 7/4. Anther color 10R 3/10 with 5Y 7/10.

*Pollen.*—Self fertile. Color varies from 5Y 8/10 to 5Y 7/10.

*Pistil.*—Number — normally 1. Surface pubescent. Average length 18.9 mm. Position of stigma an average of 1.0 mm below anthers. Color varies from 10Y 8/4 to 10Y 8/6.

*Fragrance.*—Slight.

*Color.*—Varies from 5RP 7/6 to 5RP 8/4.

*Number flowers per flower bud.*—Normally 1.

*Pedicel.*—Average length 5.4 mm. Average width 1.0 mm. Color varies from 5GY 6/6 to 5GY 4/6.

Fruit:

*Maturity when described.*—Firm ripe.

*Date of first picking.*—Jun. 7, 2010.

*Date of last picking.*—Jun. 17, 2010, varies slightly with climatic conditions.

*Size.*—Large. Average diameter axially 59.8 mm. Average transversely in suture plane 65.8 mm. Average weight 224.4 grams, average weight varies slightly with fertility of the soil, amount of thinning and climatic conditions.

*Form.*—Globose.

*Suture.*—Nearly smooth, extends from base to apex.

*Ventral surface.*—Smooth to very slightly lipped.

*Apex.*—Varies from flat to slightly retuse.

*Base.*—Retuse.

*Stem cavity.*—Rounded to slightly elongated in suture plane. Average depth 6.8 mm. Average diameter 8.1 mm.

Stem:

*Size.*—Small to medium. Average length 10.5 mm. Average diameter 3.5 mm.

*Color.*—Varies from 5GY 5/6 to 5GY 4/6.

Flesh:

*Ripens.*—Evenly.

*Texture.*—Firm, meaty.

*Fibers.*—Few, small, tender.

*Firmness.*—Very firm, firmer flesh then most commercial varieties.

*Aroma.*—Moderate.

*Amydgalin.*—Undetected.

*Eating quality.*—Very good.

*Flavor.*—Very good, mild, sweet.

*Juice.*—Moderate amount, enhances flavor.

*Brix.*—Average 10.4°, varies slightly with amount of fruit per tree and climatic conditions.

*Color.*—Varies from N 9.5/(white) to 5GY 9/1. Pit cavity color varies from 5GY 9/1 to 10GY 9/1.

Skin:

*Thickness.*—Medium.

*Surface.*—Smooth.

*Pubescence.*—Moderate amount, very short in length.

*Tendency to crack.*—None.

*Color.*—Ground color varies from 10Y 9/2 to 2.5GY 9/2, overspread with 5R 3/4 to 5R 4/10.

*Tenacity.*—Tenacious to flesh.

*Astringency.*—Undetected.

Stone:

*Type.*—Clingstone.

*Size.*—Medium to large. Average length 32.1 mm. Average width 23.9 mm. Average thickness 18.9 mm.

*Form.*—Globose.

*Base.*—Flat.

*Apex.*—Rounded to slight point. Average length 1.4 mm.

*Surface.*—Pitted throughout, pits vary from round to elongated.

*Sides.*—Unequal, one side extending further from the suture plane.

*Ridges.*—Narrow ridges running from base toward apex.

*Tendency to split.*—None.

*Color.*—Varies from 7.5YR 6/4 to 7.5YR 6/8 when dry.

Kernel:

*Size.*—Medium to large. Average width 9.8 mm. Average depth 4.4 mm.

*Form.*—Ovate.

*Taste.*—Bitter.

*Viability.*—Viable, complete embryo.

*Skin.*—Color varies from 7.5YR 7/4 to 7.5YR 7/6.

Use: Dessert.

*Market.*—Local and long distance.

Keeping quality: Good, held firm for 2 weeks at 38° to 42° F. without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree, substantially as illustrated and described.

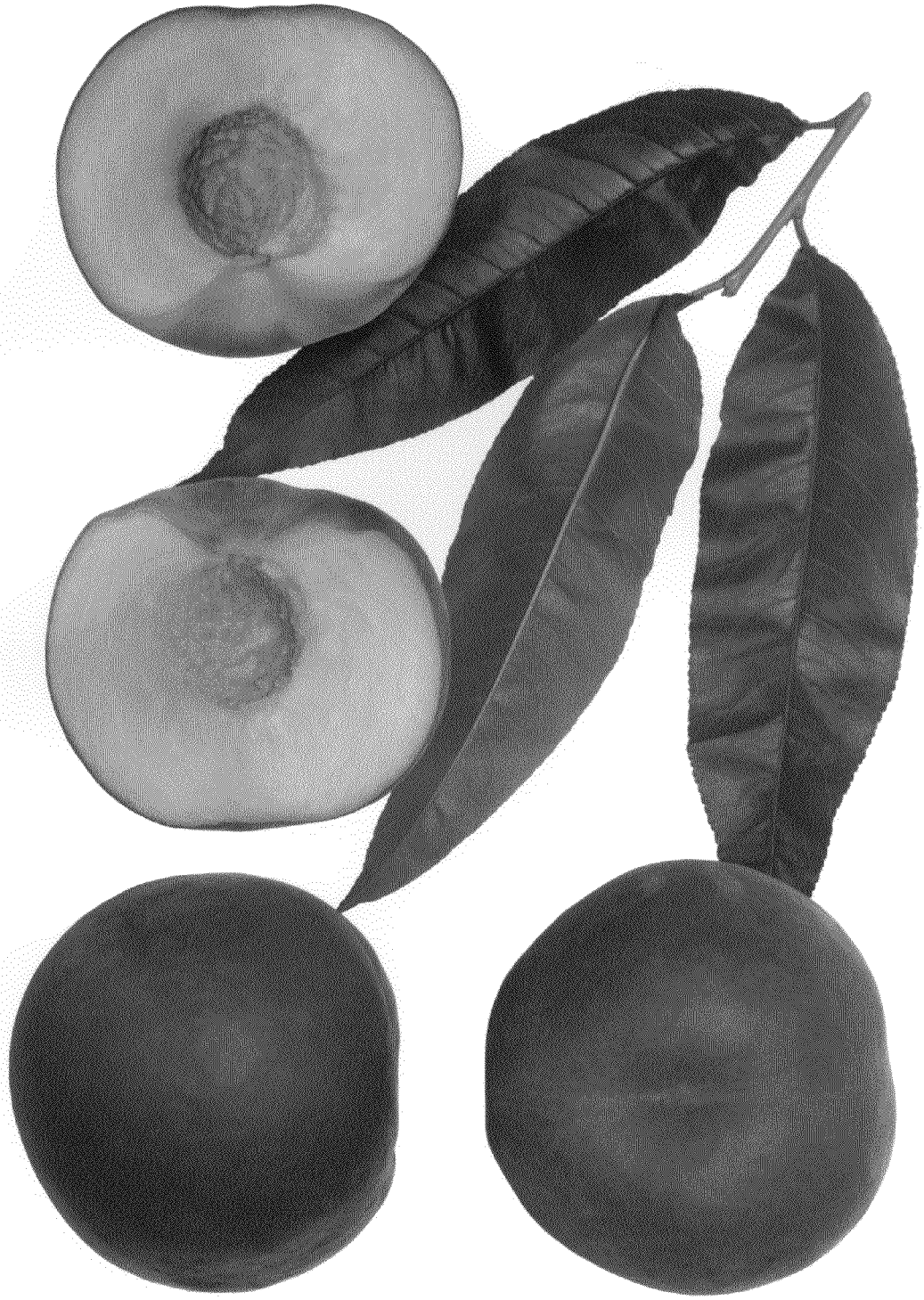

* * * * *